United States Patent [19]
Schreckendgust

[11] 3,944,387
[45] Mar. 16, 1976

[54] METHOD AND APPARATUS FOR STERILIZING WITH A HEAVIER-THAN-AIR GAS

[75] Inventor: Jay G. Schreckendgust, Pittsford, N.Y.

[73] Assignee: Sybron Corporation, Rochester, N.Y.

[22] Filed: Oct. 21, 1974

[21] Appl. No.: 516,160

Related U.S. Application Data

[63] Continuation of Ser. No. 329,722, Feb. 5, 1973, abandoned.

[52] U.S. Cl. .......................... 21/58; 21/91; 21/103; 21/104; 21/DIG. 4; 141/95
[51] Int. Cl.².. A61L 1/00; A61L 3/00; A61L 13/04
[58] Field of Search .............. 21/DIG. 4, 58, 91, 82, 21/103, 104; 141/95

[56] References Cited
UNITED STATES PATENTS

| | | | |
|---|---|---|---|
| 3,068,064 | 12/1962 | McDonald | 21/58 |
| 3,163,494 | 12/1964 | Kaye | 21/DIG. 4 |
| 3,341,280 | 9/1967 | Eolkin | 21/91 |
| 3,443,884 | 5/1969 | Linder | 21/94 |
| 3,454,352 | 7/1969 | Lamboy et al. | 21/103 |
| 3,454,353 | 7/1969 | Bjork | 21/103 |
| 3,481,692 | 12/1969 | Linder | 21/104 |
| 3,537,812 | 11/1970 | Gallagher et al. | 21/91 |

FOREIGN PATENTS OR APPLICATIONS

| | | | |
|---|---|---|---|
| 1,077,246 | 7/1967 | United Kingdom | 21/DIG. 4 |

*Primary Examiner*—Barry S. Richman
*Assistant Examiner*—Bradley R. Garris
*Attorney, Agent, or Firm*—Theodore B. Roessel; Roger Aceto

[57] ABSTRACT

Sterilizing apparatus and method in which a heavier-than-air sterilizing gas is introduced at a substantially constant flow rate into the bottom of the sterilizing chamber. Air in the chamber is displaced upwardly by the gas and out of the chamber through a restricted exhaust which is open throughout the gas introduction period. The pressure at the top of the chamber is monitored and the restricted exhaust is closed when the pressure has increased to a preselected level, the pressure level being directly related to the gas concentration. The gas inlet remains open for a time to provide a chamber pressure which will help to displace air trapped in the material being sterilized.

11 Claims, 4 Drawing Figures

METHOD AND APPARATUS FOR STERILIZING WITH A HEAVIER-THAN-AIR GAS

CROSS REFERENCE TO RELATED APPLICATIONS

This is a continuation of my earlier application Ser. No. 329,722 filed Feb. 5, 1973, and now abandoned.

BACKGROUND OF THE INVENTION

The present invention relates to a gas sterilization apparatus and method wherein a heavier-than-air sterilizing gas or gas mixture introduced into the sterilizing chamber displaces air from the chamber.

The use of a heavier-than-air sterilizing gas or gas mixture, most commonly ethylene oxide or a mixture of ethylene oxide and some diluent such as a fluorocarbon gas, is well known in the art. In certain applications, a displacement method is used to replace the air in the sterilizing chamber with sterilizing gas. In this respect, the heavier gas is introduced into the chamber and simply allowed to displace the air upwardly and out of the chamber through some top located opening. Theoretically, when the gas is introduced into the chamber, the gas and air stratify with the heavier-than-air gas settling to the bottom of the chamber and displacing the air. Thereafter, as the depth of the gas increases, the air is forced up and out of the top located opening. The sterilizing period then begins when the articles to be sterilized are submerged in the gas.

In order to insure that the articles being sterilized are submerged in the gas, the usual procedure in the prior art is to simply calculate the quantity of gas required to fill the sterilizing chamber. This given quantity of gas is then introduced into the sterilizing chamber either on a weight or a time flow basis. Such prior art methods would be completely acceptable if the gas and air stratified into a lower layer of gas and an upper layer of air wherein the interface between the two layers was exactly defined or if the load space to air space is the same for each cycle. If such were the case, a calculated amount of sterilizing gas would replace a similar calculated amount of air so that the sterilizing chamber could be completely filled with the sterilizing gas and the air completely displaced.

As a practical matter, however, an intermediate layer forms between the sterilizing gas in the bottom of the sterilizer and the air in the top of the sterilizer. This intermediate layer is a mixture of air and the sterilizing gas. There are several factors which could lead to the formation of such an intermediate layer. For example, any turbulence created as the sterilizing gas enters the chamber will result in mixing of the gas and air. Also, any temperature differential between the articles being sterilized and the chamber may set up convection currents within the sterilizer which mixes the gas and the air. A third factor is termed "diffusion mixing" wherein the air and gas molecules tend to diffuse across the boundary between the upper layer of air and lower layer of gas. In any event, it is recognized that a relatively large and often variable intermediate layer, of a air-gas mixture forms between the layer of air and the lower layer of gas. Consequently, the prior art recognizes that a given volume of gas, no matter how carefully it is introduced into the sterilizing chamber, will not displace an equal amount of air.

To compensate for this, the prior art may employ some sort of gas monitor, analyzer or "presence of" detector to examine the exhaust of the chamber and indicate when there is sterilizing gas present in the air being displaced from the sterilizer. Depending upon the articles being sterilized, the introduction of gas can be stopped when sterilizing gas is just detected in the exhaust or when a particular concentration of sterilizing gas in the exhaust is reached. It should be readily appreciated that any such monitor, analyzer or presence of detector adds greatly to the cost of the sterilizing equipment.

A less expensive method to insure that articles being sterilized are completely submerged in the gas is to introduce an excess of gas into the sterilizing chamber. This method, however, is inherently inaccurate as the conditions which lead to the formation of the intermediate layer may vary from cycle to cycle and what may be an excess of sterilizing gas under one set of conditions may not be an excess under a slightly different set of conditions.

In the present invention, the sterilizing gas is introduced into the sterilizing chamber at a substantially constant flow rate. A low impedance restrictor is located in the exhaust to impede the passage of air and gas displaced from the chamber. Since the density of the sterilizing gas is greater than air, the gas exhibits different drag characteristics when flowing through the restrictor than does air, and it can be demonstrated that the flow rate of gas and displaced air leaving the sterilizing chamber through the restrictor is inversely proportional to the square of their densities. Because of these different drag characteristics, it has been experimentally verified that one equilibrium pressure level is established in the chamber during the time that only air is being displaced through the restricted exhaust and another higher pressure when only gas is passing through the restricted exhaust. When the intermediate layer, which is a mixture of gas and air, is displaced through the restrictor, the pressure in the chamber increases in direct proportion to an increase in gas concentration in the intermediate layer. Thus, at a constant input rate the pressure within the chamber can be directly correlated to the concentration of sterilizing gas within the chamber.

SUMMARY OF THE PRESENT INVENTION

The method and apparatus of the present invention may be characterized in one aspect thereof by providing means for introducing a heavier-than-air sterilizing gas into a sterilizing chamber at a substantially constant flow rate wherein the gas and air tend to stratify in the chamber forming a lower layer of gas, an upper layer of air and an intermediate layer of a gas-air mixture, the layer of air and the upper end of the intermediate layer being displaced out of an open exhaust as the depth of the gas layer increases; maintaining a restriction in the open exhaust during the introduction of gas; and monitoring the pressure of the sterilizing chamber and closing both the gas inlet and restricted exhaust when the pressure has reached a pre-selected level.

OBJECTS OF THE INVENTION

One object of the present invention is to provide a low cost, easily operated, fill detector for gas sterilizing systems.

Another object of the present invention is to provide a gas sterilization method and apparatus for detecting when air in the sterilizing chamber has been replaced by the desired concentration of sterilizing gas.

A further object of the present invention is to provide a gas sterilizing apparatus and method wherein the introduction of sterilizing gas is automatically terminated upon the attainment of a desired gas concentration level within the sterilizing apparatus.

A still further object of the present invention is to provide a gas sterilizing method and apparatus wherein the desired concentration of sterilizing gas is established and maintained substantially constant throughout the sterilizing cycle.

A yet further object of the present invention is to provide a gas sterilization apparatus and method wherein the air in the chamber is replaced by the sterilizing gas in such a manner that the concentration of gas in the chamber is directly proportional to the pressure in the chamber, the introduction of gas being terminated when a predetermined pressure level is reached.

These and other objects and advantages and characterizing features of the present invention would become more apparent upon consideration of the following detailed description thereof when taken in connection with accompanying drawings depicting the same.

DESCRIPTION OF THE PREFERRED EMBODIMENTS

Figure 1:
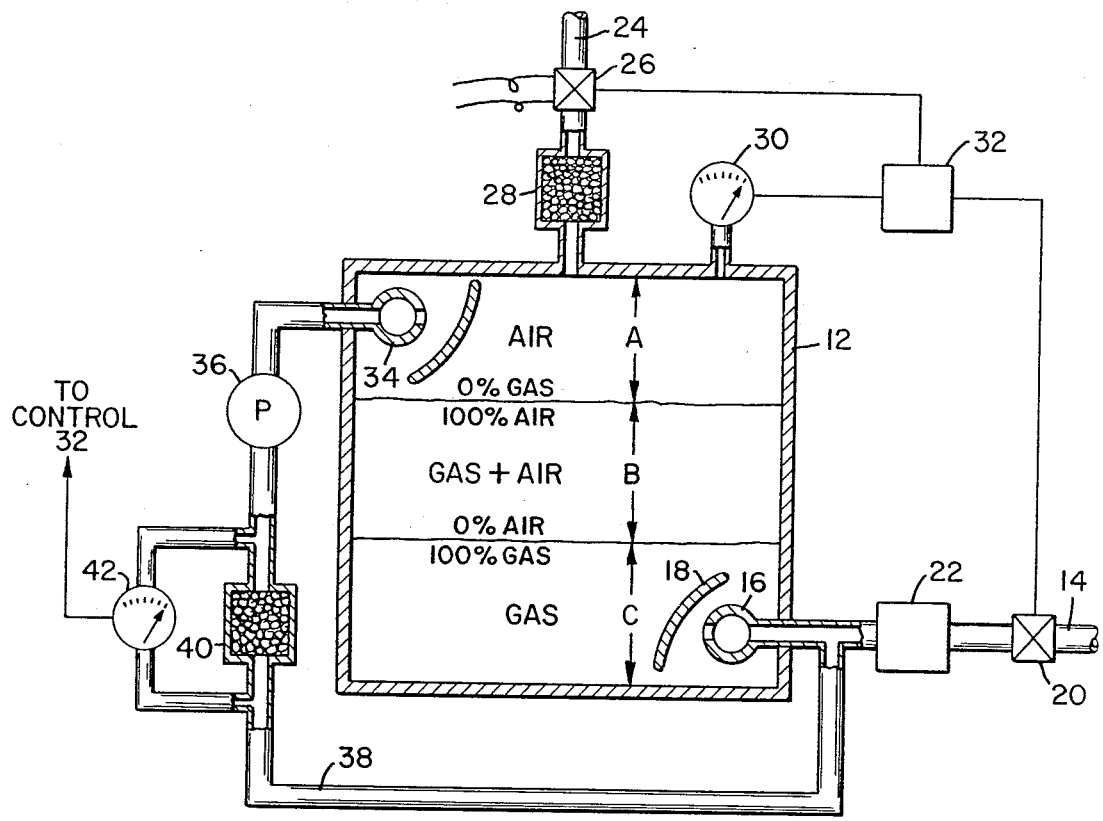
FIG. 1 is a schematic representation of the sterilizing apparatus of the present invention.

Referring to the drawings, FIG. 1 is a schematic representation of the apparatus as may be employed in the present invention. The apparatus includes a sterilizing chamber 12 into which are placed the articles (not shown) to be sterilized. A sterilizing gas such as ethylene oxide or a mixture of ethylene oxide and some inert gas is delivered to the chamber from a source not shown through a gas inlet line 14. The gas inlet line terminates in a manifold 16 within the sterilizing chamber. This manifold together with a baffle member 18 which may be of a type commonly employed in the art, reduces turbulence as the gas is introduced into the sterilizing chamber. The gas inlet line is opened and closed by a solenoid valve 20 and flow of the gas into the chamber is controlled by a regulator 22. The regulator, also of a type well-known in the art, reduces surging at the input line in order to obtain a constant input flow of sterilizing gas which also reduces input turbulence.

As shown in FIG. 1, the gas entering the sterilizer and the air in the sterilizer tend to stratify according to their densities. The heavier gas is in a lower layer C, the lighter air in an upper layer A with an intermediate layer B being made up of an air-gas mixture. It should be appreciated that there is no well defined boundary between the three layers as schematically illustrated in FIG. 1. Actually, the intermediate layer has a concentration of gas which decreases and an air concentration which increases from the bottom of the layer to the top.

The top of the sterilizing chamber is provided with an outlet or exhaust 24 which is opened and closed by a solenoid valve 26. As gas is being introduced through line 14, exhaust solenoid valve 26 remains open to permit the displacement of the upper air layer A from the chamber. A resistor 28 is provided in the exhaust for purposes set out hereinbelow.

Also communicating with the top of sterilizing chamber 12 is a pressure sensitive device 30 which may include a pressure gauge and recording chart. This device is connected to a control means 32, which is in turn connected to gas inlet solenoid valve 20 and exhaust solenoid 26.

As set forth hereinabove, there is a restrictor 28 in exhaust line 24. The function of this restrictor is to impart a drag force to the air and sterilizing gas flowing through the exhaust. While various restrictor designs may impart a suitable drag force to the air and gas, the restrictor found suitable for a 24 cubic foot sterilizer with gas input rates of between 1–2 CFM was a cylinder 25 mm in diameter and 250 mm long. The restrictor was packed with glass spheres 2.5 mm in diameter.

Figure 2:
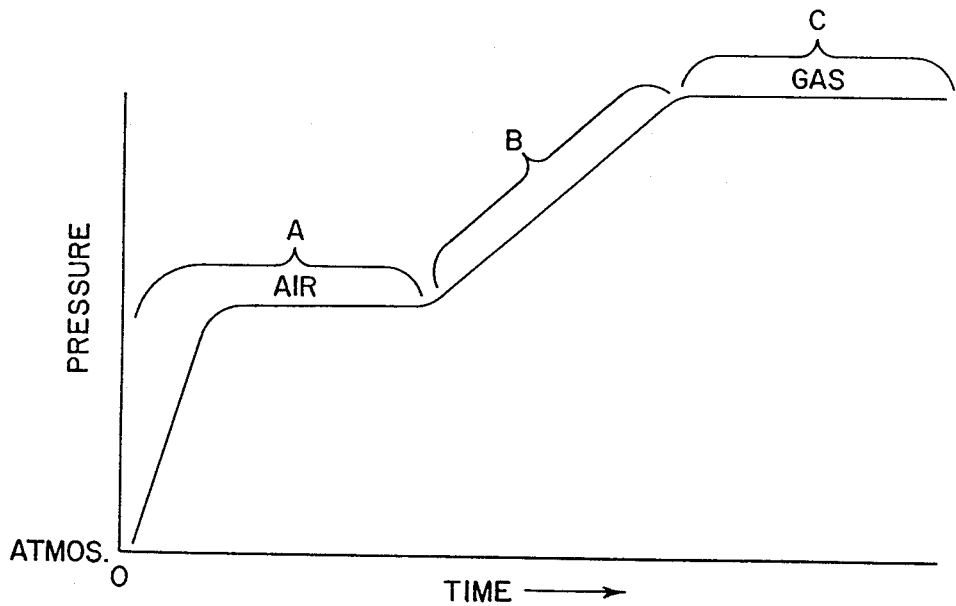
FIG. 2 is a graph showing the pressure-time relationship for a typical sterilizing chamber during the fill or air displacement portion of the sterilizing cycle.

Imparting sufficient drag to the air and gas passing through the restrictor is important to the present invention because it is known from gas dynamics that under conditions of constrained constant flow the pressure of two gases will be directly proportional to their densities. Accordingly, if sterilizing gas is introduced into the chamber at a controlled constant flow, the drag on the air passing through the restrictor will be different than the drag on the gas passing through the restrictor. Consequently, the pressure in the chamber as indicated by gauge 30 will be at one value when just air is flowing through the restrictor and a higher value when just gas is flowing through the restrictor. This is illustrated by the graph shown in FIG. 2.

Starting the introduction of gases in the chamber at time 0 and with the chamber at atmospheric pressure, the graph shows that the pressure in the chamber quickly rises to a first equilibrium level at A. During this time, a steady state condition is established wherein gas entering the chamber displaces air in the upper layer A at the same rate. The drag on the air produced by restrictor 28 quickly reaches and stablizes at a constant value slightly higher than atmospheric. As intermediate layer B of the gas and air mixture begins passing through the restrictor, the drag produced by the restrictor on the gas component of the intermediate layer starts to become evident and the pressure in the chamber begins to rise gradually as shown in section B of the curve.

As set out above, the gas concentration decreases and the air concentration increases from the bottom of the intermediate layer B to the top. For this reason, the pressure in the chamber gradually rises as intermediate layer B passes through the restrictor and a greater and greater concentration of gas flows through the restrictor. When all of the air in layer A and substantially all of the intermediate layer B has been displaced out of the chamber and only gas flows through the restrictor, a second steady state condition is established as shown at C in FIG. 2.

Figure 3:
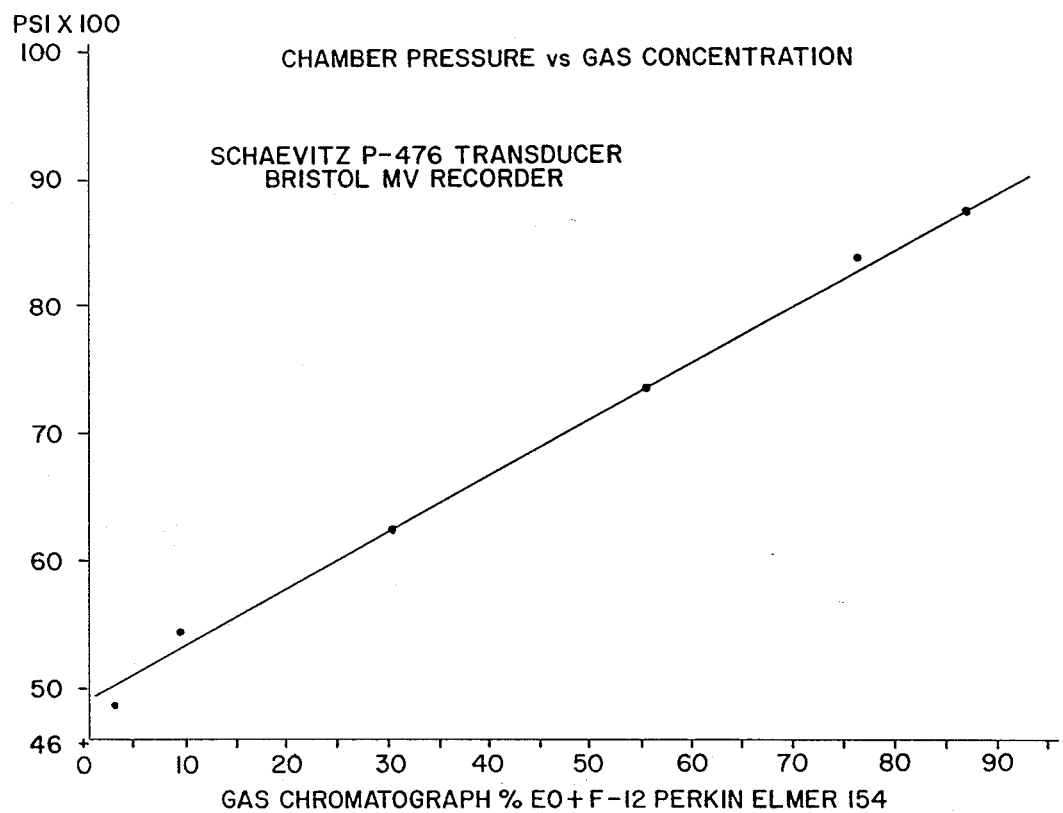
FIG. 3 is a graph showing the correlation between pressure and actual ethylene oxide concentration during a typical sterilizing cycle.

Actual tests have shown the direct correlation between the pressure within the sterilizing chamber and the concentration of sterilizing gas. This is illustrated in FIG. 3 which shows portion B of the graph FIG. 2 on the larger scale. To demonstrate this correlation, a Perkin Elmer gas chromatograph was set up to monitor the exhaust from the chamber at various time intervals. The pressure in the chamber was continuously monitored by a Shaevitz transducer and the pressure recorded with a Bristol recorder. The solid line represents the pressure as traced by the Bristol recorder and the points on the line represents plots of the gas concentration as measured periodically by the gas chromatograph. As clearly illustrated, the plot of the gas concentration fall on the trace of the pressure and establishes a correlation between the pressure in the sterilizing chamber and the sterilizing gas concentration. Repeat runs on different days with different loads and using the same input flow rates of sterilizing gas showed deviation of less than 2% of the gas concentration shown in FIG. 3.

Knowing the correlation between chamber pressure and concentration of sterilizing gas, the apparatus shown in FIG. 1 may be programmed to terminate the introduction of gas when the desired concentration is reached. In this respect, the desired gas concentration or pressure which corresponds to the desired gas concentration is set on control 32. When the sterilizing cycle begins control 32 simply opens both gas inlet solenoid 20 and exhaust solenoid 26. The sterilizing gas is introduced into the sterilizing chamber at a constant flow rate as established by regulator 22. When the pressure within the chamber, as determined by sensor 30 has reached the preset level, controller 32 will operate to close both the gas inlet and the exhaust valves for a time sufficient to sterilize the articles within the chamber at the concentration of gas which has been selected.

For any given input flow rate the time that it takes to reach the desired concentration will depend upon the size of the load. As an example of this and also to demonstrate the automatic control and the ability of the present invention to adapt to various load sizes, two runs on the same sterilizer were made. The sterilizer used for both runs had a capacity of 24 cubic feet. The gas during each run was introduced at the rate of one cubic foot per minute. In the first run, the load occupied only 0.85 cubic feet of the sterilizer or approximately 4.8% of theoretical load capacity. For this first run, the automatic shut-off of the exhaust occurred 14 minutes after the start of the cycle. The second run was made with a load which occupied approximately 16 cubic feet of the sterilizer or about 38.4% of capacity. For this run the automatic shut-off occurred in 9 minutes. The runs were repeated on another day with the concentration of gas for each run being within 3% of the previous runs.

Figure 4:
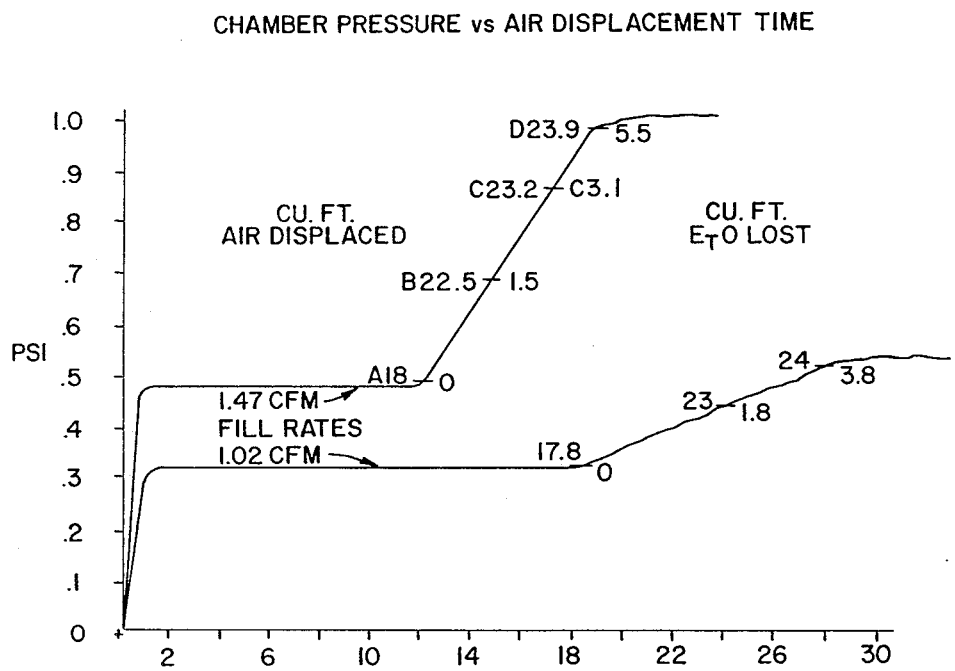
FIG. 4 is a graph showing a family of curves illustrating fill time for different input flow rates.

Since the correlation between chamber pressure and concentration of sterilizing gas for any given input rate of the sterilizing gas is reproducable, a family of curves such as shown for example in FIG. 4 can be provided with each apparatus. The two curves shown in FIG. 4 are both for a 24 cubic foot sterilizer. With the information contained in these curves, the operator would be able to select the flow rate most economical to his particular sterilizing operation. For example, if in the particular sterilizing procedure being employed, time is a more critical factor than the amount of ethylene oxide lost, the operator would select the high fill rate. In this respect, FIG. 4 shows, that a fill rate of 1.47 cubic feet per minute will displace substantially 100% of the air from the sterilizing chamber at a loss of 5.5 cubic feet of ethylene oxide. The lost ethylene oxide is that portion of the gas mixed with the air in the intermediate layer which must be the displaced in order to have substantially 100% gas in the chamber.

On the other hand, if time is not a factor and the operator wishes to economize on the amount of ethylene lost during the sterilizing cycle, a lower fill rate would be selected. In this respect, the second curve shows that a fill rate of 1.02 cubic feet per minute displaces substantially all of the air from the sterilizer in approximately 28 minutes with a loss of only 3.8 cubic feet of ethylene oxide.

Thus, far, the invention has been described only in connection with terminating the introduction of sterilizing gas when a predetermined pressure level is reached in the sterilizing chamber, the pressure level being correlated to a concentration of ethylene oxide at a given input flow rate. However, the present invention may also be adapted to maintain the gas concentration relatively constant during the gas diffusion phase of the sterilizing cycle. For example, if the articles to be sterilized are sealed in packages made of a material which is permeable to the sterilizing gas, sterilization of the article is accomplished by replacing the air in the package with the gas. This replacement is accomplished by diffusion of the gas and air across the package material. Even though a desired gas concentration has been reached, the gas within the sterilizing chamber is diluted slightly as the air in the packages diffuses out of the package and into the chamber. The present invention can be readily adapted to compensate for this dilution by admitting additional sterilizing gas into the chamber to restore the initial gas concentration.

To do this, the apparatus, as shown in FIG. 1, includes an intake manifold 34 adjacent the top of the sterilizing chamber. This manifold is connected to the intake of a pump 36. The outlet of the pump is connected through a line 38 to the gas inlet manifold. Located in line 38 is a restrictor 40 which functions in a manner similar to restrictor 28. Pressure sensing means 42 located across the restrictor is connected through control means 32 to the gas inlet solenoid 20.

In operation, and beginning after gas inlet solenoid 20 and the exhaust solenoid 26 are closed, pump 36 will begin circulating the sterilizing gas in the chamber. The gas is drawn into intake manifold 34, pumped through restrictor 40 in line 38 and back into the sterilizing chamber through manifold 16. The pressure drop, measured by sensor 42 across the restrictor, is indicative of the gas concentration in the sterilizing chamber. As the gas is diluted by air diffusing out of the packages being sterilized, the pressure across restrictor 40 will decrease. When the pressure has dropped to a predetermined level as sensed by pressure sensor 42, control 32 will cause gas inlet solenoid 20 to open. The gas now indroduced into the sterilizing chamber will bring the gas concentration back to desired level. When this level is reached and indicated by an increase in the pressure drop across restrictor 40, control 32 will close the gas inlet solenoid. In this manner the inlet solenoid can be cycled on and off throughout the gas diffusion stage of the sterilizing cycle in order to maintain the concentration of gas within the sterilizer at a fairly constant value.

Thus it should be appreciated that the present invention accomplishes its intended objects in providing a simple and effective means for indicating when the desired concentration of sterilizing gas is present in the sterilizing chamber and which maintains the gas at the desired concentration throughout the sterilizing cycle.

Having thus described the invention in detail, what is claimed as new is:

1. In a gas sterilizing method, the steps for replacing air in a sterilizing chamber with a heavier-than-air sterilizing gas comprising:
   a. introducing said gas into said chamber adjacent the bottom thereof at a substantially constant flow rate;
   b. maintaining an open exhaust adjacent the top of said chamber, the air within said chamber being displaced upwardly by said heavier-than-air gas and said air and gas passing through said open exhaust in such a manner that a detectable drag force is created on the air and gas passing through said open exhaust so that pressure in the chamber when just air is passing through said exhaust remains at a first substantially constant level which is lower than a second substantially constant level when just sterilizing gas is passing through said exhaust.
   c. monitoring the pressure in said chamber with a pressure sensor during said gas introduction step and while said exhaust is open, said pressure being correlated to the concentration of gas in said chamber, and
   d. closing said exhaust during said gas introduction step in response to an indication by said pressure sensor that the pressure and therefore the gas concentration in said chamber has reached a predetermined level.

2. In a gas sterilizing method wherein the articles to be sterilized are maintained in a closed chamber containing a heavier-than-air sterilizing gas for a timed period sufficient to effect sterilization, the improvement comprising:
   a. circulating said gas in said closed chamber during said timed period by pumping said gas through a restrictor means at a constant flow rate;
   b. monitoring the pressure drop across said restrictor means; and
   c. introducing additional amounts of gas into said chamber when said pressure drop across said restrictor means falls below a predetermined level.

3. The method as set forth in claim 2 wherein circulating said gas is accomplished by pumping said gas from said chamber through a restrictor means exterior of said chamber and then back into said chamber.

4. In a method for sterilizing articles in a sterilizing chamber including replacing the air in the chamber with a heavier-than-air sterilizing gas, the improvement comprising the steps of:
   a. introducing said sterilizing gas into the bottom of said chamber at a substantially constant flow rate, said sterilizing gas and the air in said chamber tending to stratify into a lower layer of sterilizing gas, an upper layer of air and an intermediate layer of a sterilizing gas-air mixture;
   b. maintaining an open exhaust outlet at the top of said chamber during the introduction of said sterilizing gas, wherein said upper layer of air and said intermediate layer are displaced upwardly in said chamber by said lower layer of sterilizing gas and out through said open exhaust outlet;
   c. creating a detectable drag force on the air and sterilizing gas passing through said open exhaust outlet so that pressure in the chamber when just air is passing through said exhaust outlet remains at a first substantially constant level which is lower than a second substantially constant level when just sterilizing gas is passing through said exhaust outlet, the pressure intermediate said levels being in direct proportion to the concentration of said sterilizing gas in said intermediate layer;
   d. monitoring the pressure in said chamber with a pressure sensor adjacent said exhaust outlet during said sterilizing gas introduction step;
   e. closing said exhaust outlet in response to an indication by said pressure sensor that the pressure in the chamber has reached a predetermined level higher than said first substantially constant level; and
   f. stopping the introduction of gas and thereafter maintaining the articles in said chamber for a time period sufficient to effect the sterilization of the articles.

5. A method as set forth in claim 4 wherein step (e) occurs when the pressure in said chamber is at a level intermediate said first and second substantially constant levels.

6. The method as set forth in claim 4 including the steps of:
   g. circulating the gas in said sterilizing chamber during at least a portion of the time period of step (f) by pumping the gas through a restrictor means at a constant flow rate;
   h. monitoring the pressure drop across the restrictor means; and
   i. introducing additional amounts of the sterilizing gas into said sterilizing chamber when said pressure drop across the restrictor means falls below a predetermined level.

7. The method as set forth in claim 6 wherein circulating said gas is accomplished by pumping said gas from said chamber through a restrictor means exterior of said chamber and then back into said chamber.

8. In a gas sterilizing apparatus including a sterilizing chamber, gas inlet means adjacent the bottom of said chamber for introducing a heavier-than-air sterilizing gas at a constant flow rate into said chamber and an exhaust means adjacent the top of said chamber for venting said chamber, the improvement comprising:
   a. restrictor means in said exhaust means impeding the passage of air and gas therethrough for imparting a drag to the air and gas displaced and vented from said chamber during the introduction of said gas, the drag imparted to venting gas being greater than the drag imparted to venting air by reason of the density of said gas being greater than that of air;
   b. pressure sensor means operative during the period of gas introduction for monitoring the pressure in said chamber created by the action of said restrictor means impeding the venting of air and gas, the pressure in said chamber under conditions of constant flow of gas into/and displacement from said chamber being correlated to the concentration of gas in said chamber; and
   c. control means maintaining said exhaust means open during introduction of gas into said chamber and closing said exhaust means in response to an indication by said pressure sensor that the pressure and therefore, the concentration of gas in said chamber has reached a predetermined level.

9. Apparatus as set forth in claim 8 including:
   d. means operable after both said inlet means and exhaust means are closed to circulate the gas in said sterilizing chamber at a constant flow through a second flow restrictor means;
   e. means monitoring the pressure drop across said second flow restrictor means; and f. means acting responsive to a reduction in said pressure drop for opening said gas inlet means.

10. In a gas sterilizing apparatus including a sterilizing chamber, gas inlet means for introducing a heavier-than-air sterilizing gas into said chamber and an exhaust means for venting said chamber, the improvement comprising:
   a. flow restrictor means in communication with said chamber;
   b. means operable after both said inlet means and exhaust means are closed to circulate the gas in said chamber at a constant flow rate through said flow restrictor means;
   c. means monitoring the pressure drop across said flow restrictor means; and
   d. means acting responsive to a reduction in said pressure drop for opening said gas inlet means.

11. Gas sterilizing apparatus comprising:
   a. a sterilizing chamber having an outlet adjacent the top thereof;
   b. means for introducing a heavier-than-air sterilizing gas into the bottom of said chamber at a substantially constant flow rate, the gas and air in said chamber tending to form an upper layer of air, a lower layer of gas and an intermediate layer of an air-gas mixture, the gas concentration decreasing from the bottom to the top of said intermediate layer;
   c. restriction means in said outlet impeding the passage of air and gas therethrough for imparting a drag to the air and gas displaced and vented from said chamber during the introduction of said gas, the drag imparted to venting gas being greater than the drag imparted to venting air by reason of the density of said gas being greater than that of air;
   d. means maintaining said outlet open during the introduction of said heavier-than-air gas to permit an upward displacement out of said chamber of said upper air layer and at least part of said intermediate layer;
   e. pressure sensor means operable during gas introduction for monitoring the pressure in said chamber created by said restriction means, the pressure in said chamber under conditions of constant flow of said gas during introduction into and displacement out of said chamber being directly proportional to the concentration of gas in the effluent passing through said outlet; and
   f. means closing said outlet in response to said pressure sensor means when the pressure in said chamber during the introduction of gas and displacement of air reaches a predetermined level corresponding to a desired gas concentration.

* * * * *